United States Patent
Zhu et al.

(10) Patent No.: US 12,154,269 B2
(45) Date of Patent: Nov. 26, 2024

(54) EXTRACTION METHOD FOR RADIOMICS FEATURE INFORMATION OF KNEE JOINT EFFUSION

(71) Applicant: Zhujiang Hospital of Southern Medical University, Guangdong (CN)

(72) Inventors: Zhaohua Zhu, Guangdong (CN); Qiushun Bai, Guangdong (CN); Jieying Chen, Guangdong (CN); Yuping Zeng, Guangdong (CN); Qiang Song, Guangdong (CN); Changhai Ding, Guangdong (CN)

(73) Assignee: Zhujiang Hospital of Southern Medical University, Guangzhou (CN)

( * ) Notice: Subject to any disclaimer, the term of this patent is extended or adjusted under 35 U.S.C. 154(b) by 444 days.

(21) Appl. No.: 17/483,747

(22) Filed: Sep. 23, 2021

(65) Prior Publication Data
US 2022/0092777 A1    Mar. 24, 2022

(30) Foreign Application Priority Data
Sep. 23, 2020  (CN) .......................... 202011007326.9

(51) Int. Cl.
*G06T 7/00*  (2017.01)
*A61B 6/00*  (2006.01)
*A61B 6/50*  (2024.01)

(52) U.S. Cl.
CPC ............ *G06T 7/0012* (2013.01); *A61B 6/505* (2013.01); *A61B 6/5241* (2013.01); *G06T 2207/10088* (2013.01); *G06T 2207/30008* (2013.01)

(58) Field of Classification Search
CPC ........ G06T 7/0012; G06T 2207/10088; G06T 2207/30008; G06T 2207/20076;
(Continued)

(56) References Cited

U.S. PATENT DOCUMENTS 10,872,408 B2 * 12/2020 MacKinnon ......... A61B 5/4528
10,991,097 B2 *  4/2021 Yip ........................... G06T 7/11
(Continued)

FOREIGN PATENT DOCUMENTS

| CN | 110390665 A | 10/2019 |
| CN | 111383218 A | 7/2020 |

OTHER PUBLICATIONS

S. Rastegar et al. "Radiomics for classification of bone mineral loss: A machine learning study" (hereafter Rastegar). (Year: 2020).*

*Primary Examiner* — Dhaval V Patel

(57) ABSTRACT

The disclosure belongs to the technical field of radiomics, and particularly relates to an extraction method for radiomics feature information of knee joint effusion. each layer of an image is segmented into a plurality of regions, the interference of image noises in each region is removed, then whether each region after interference removal is an effusion region or not is judged, finally, the radiomics features of each effusion region are calculated, interpolation processing is respectively implemented on the obtained image position and the area of the effusion regions, an effusion area simulation change curve is drawn, curve integration is implemented to obtain volume information, and all the extracted information is stored in a cell array of a MATLAB. thus the effusion information in the MRI image of the knee joint is automatically extracted, and meanwhile, the method is fast in speed, high in accuracy, good in repeatability.

12 Claims, 6 Drawing Sheets

(58) Field of Classification Search
CPC .. G06T 7/136; G06T 7/45; G06T 7/62; G06T 7/11; A61B 6/505; A61B 6/5241; G06F 18/24; G06V 10/40
See application file for complete search history.

(56) References Cited

U.S. PATENT DOCUMENTS

| | | | |
|---|---|---|---|
| 11,443,428 B2* | 9/2022 | Petersen | G06T 7/11 |
| 11,636,602 B1* | 4/2023 | Havír | G06V 10/774 |
| | | | 382/164 |
| 2004/0068523 A1* | 4/2004 | Keith, Jr. | G06F 16/1787 |
| 2013/0336553 A1* | 12/2013 | Buisseret | G06T 7/13 |
| | | | 382/128 |
| 2017/0202520 A1* | 7/2017 | Urish | A61B 5/055 |
| 2020/0126656 A1* | 4/2020 | Vincent | G16H 50/50 |

* cited by examiner

EXTRACTION METHOD FOR RADIOMICS FEATURE INFORMATION OF KNEE JOINT EFFUSION

CROSS REFERENCE TO RELATED APPLICATIONS

The present application claims the benefit of Chinese Patent Application No. 202011007326.9 filed on Sep. 23, 2020, the contents of which are incorporated herein by reference in their entirety.

TECHNICAL FIELD

The disclosure belongs to the technical field of radiomics, and particularly relates to an extraction method for radiomics feature information of knee joint effusion.

BACKGROUND

Osteoarthritis is the most common osteoarticular disease worldwide with the largest number of patients, the total prevalence rate of the population is about 15%, the disease course is long, great pain is brought to the patients, and knee is the most commonly affected joint. Joint replacement surgery is often needed in the late stage of osteoarthritis, causing heavy economic and social burdens. Knee joint effusion is a typical pathological change of osteoarthritis, and is closely related to disease severity and joint pain. However, the assessment of knee joint effusion mainly depends on clinical experience of doctors at present, and quantitative measurement evaluation is not yet clinically available, which has hindered the development of diagnosis and treatment of knee osteoarthritis. A related image processing software, OsiriX, can integrate Magnetic Resonance Imaging (MRI) image data to generate a 3D image so as to facilitate observing and measuring of maximum effusion area and volume. But this tool is only supported by Mac OX operating system and provide semi-automatic measurement. In other words, the effusion area in each page of MRI needs to be manually drawn, which is rather time consuming (more than 15 minutes on average for each patient). Besides, the cost is high, and the feasibility of actual clinical application is poor.

SUMMARY

In order to solve the problems, the disclosure provides an extraction method for radiomics feature information of knee joint effusion, which may be used for quantitatively and automatically extracting information on volume and area of effusion as well as various radiomics information of magnetic resonance (MR) on knee joint. Meanwhile, the method is fast in speed, high in accuracy, good in repeatability, free of platform limitation, and may be used for clinical diagnosis of knee osteoarthritis and prediction of disease progression and prognosis.

To solve the above technical problems, the disclosure adopts the following technical solution.

An automatic extraction method for radiomics features of knee joint based on a MATLAB is provided. First, each layer of an image is segmented into a plurality of regions, the interference of image noises in each region is removed, then whether each region after interference removal is an effusion region or not is judged, finally, radiomics features of each effusion region are calculated. Meanwhile, interpolation processing is respectively implemented on the obtained image position and the effusion areas, an effusion area simulation change curve is drawn, then curve integration is implemented to obtain volume information, and all the extracted information is stored in a cell array of the MATLAB.

Furthermore, the method includes the following steps.

In a1, image data is prepared.

In a2, content of a folder is acquired and judged.

In a3, an image sequence is analyzed, and an extraction mode is automatically selected.

In a4, radiomics features of effusion is extracted, which specifically refers to: first, each layer of an image is segmented into a plurality of regions, the interference of the image noises in each region is removed, then whether each region after interference removal is an effusion region or not is judged, finally, radiomics features of each effusion region are calculated. Meanwhile, interpolation processing is respectively implemented on the obtained image position and area of the effusion areas, an effusion area simulation change curve is drawn, then integration is implemented to obtain volume information, and all the extracted information is stored in a cell array of the MATLAB.

Furthermore, the operation that each layer of an image is segmented into a plurality of regions, and the interference of image noises in each region is removed specifically includes that: first, filtering the image, entering a first layer, the first layer is segmented into a plurality of regions with a low threshold value, then the interference of the image noises in each region is removed by implementing opening operation in morphological operation, if the number of the regions obtained in the first layer is greater than a set value, entering the next layer, finally, a second layer is segmented into a plurality of regions with a high threshold value, the interference of the image noises in each region is removed by implementing opening operation in morphological operation, if the number of the regions obtained in the second layer is greater than a set value, entering the next image layer, and so on, until all the layers of the image are processed.

Furthermore, the operation that whether each region after interference removal is an effusion region or not is judged specifically refers to: at least one of the following judgments is implemented on each obtained region after interference removal.

When the ratio of the area to the perimeter of the region is smaller than or equal to a set value, the region is judged as a subcutaneous fat region, and when the ratio of the area to the perimeter of the region is greater than the set value, the region is judged as an effusion region.

When a third-order moment of the region is smaller than a set value, the region is judged as an effusion region, and when the third-order moment of the region is greater than or equal to the set value, the region is judged as a subcutaneous fat region, and the formula of the third-order moment is as follows.

$$\zeta_i = \left[ \frac{1}{N} \sum_{j=1}^{N} (P_{ij} - \mu_i)^3 \right]^{1/3}$$

$\zeta_i$ refers to the third-order moment of the i region, N is the total number of pixels of the i region, $$\mu_i = \frac{1}{N}\sum_{j=1}^{N} P_{ij},$$

$P_{ij}$ refers to the gray value of the jth pixel of the i region.

Furthermore, the operation that when the ratio of the area to the perimeter of the region is smaller than or equal to a set value specifically refers to: the set value of the first layer is 4.5, the set value of the second layer is 10, and in the operation that when the third-order moment of the region is smaller than a set value, the set value is 0.

Furthermore, in the operation that the radiomics features of each effusion region are calculated, the radiomics features include gray level features and gray level co-occurrence matrix features; and the gray level features include area, contrast ratio, maximum value, average value, standard deviation, smoothness, third-order moment, consistency and entropy, and the gray level co-occurrence matrix features include contrast ratio, correlation, energy, co-occurrence degree and entropy.

Furthermore, the operation that interpolation processing is respectively implemented on the obtained image position and area of the effusion areas, and an effusion area simulation change curve is drawn specifically refers to: the positions of a plurality of obtained images and the effusion areas are processed, a coordinate system is established by taking a value obtained after interpolation processing of the shot depth as an x axis and taking a value obtained after interpolation processing of the measured area as a y axis, and the effusion area simulation change curve is obtained.

Furthermore, the operation that curve integration is implemented to obtain volume information specifically refers to: volume information is obtained through calculating according to formula $V=\int_0^d area(x)dx$, d is the thickness of the knee joint, and area (x) is an area function obtained after interpolation.

Furthermore, the operation of a1, image data is prepared refers to the image sequence is stored in a single folder, and the requirements of the image sequence are as follows: 1, the image is obtained by a single examination of a patient, 2, the image is an MRI PDW coronal image of the knee joint, 3, the length of the sequence is not limited, and 4, the image resolution is not limited.

The operation that "content of a folder is acquired and judged" refers to a user inputs the address of the folder in Graphical User Interface (GUI) generated by MATLAB, and clicks and loads, then a system acquires information of the folder and makes judgment, and the judgment process is as follows.

In a201, a directory under the folder is read for the first time.

In a202, whether the obtained first directory is the previous directory or not is judged, and if so, step a3 is executed according to the directory obtained for the first time; otherwise, step a3 is executed according to the address of the folder.

A system acquires information of the folder, the information refers to information acquired from the image, including an image gray level matrix and metadata, and the metadata includes but is not limited to case basic information, shooting parameters, time and position information of the image.

Furthermore, the operation that an image sequence is analyzed, and an extraction mode is automatically selected specifically refers to: a first image is acquired, if the first image meets the condition, the extraction mode is set to be 1, and otherwise, the extraction mode is set to be 0; and the condition refers to that the area of a region obtained by implementing threshold segmentation on the global region with a low threshold value is greater than a set value.

The disclosure mainly has the following beneficial effects.

Through the above technical solution, magnetic resonance may be implemented on the knee joint, meanwhile, the volume and area of the effusion and various radiomics information may be quantitatively and automatically extracted, so that information of effusion in the MRI image of the knee joint is automatically extracted. Meanwhile, the method is fast in speed, high in accuracy, good in repeatability and free of platform limitation. The extracted volume and area of the effusion may be used for clinical diagnosis of knee osteoarthritis and prediction of disease progression and prognosis, the extracted radiomics information may be used for constructing an accurate disease transformation prediction model or other scientific researches related to radiomics, and the method is worth being popularized in the field of magnetic resonance image research.

DETAILED DESCRIPTION OF THE EMBODIMENTS

In order to make the purpose, technical solutions and advantages of the disclosure clearer, the disclosure will be further described below in combination with the drawings and embodiments. It is to be understood that the specific embodiments described herein are for the purpose of explaining the disclosure only and are not intended to limit the disclosure.

The disclosure will be further described below in combination with the drawings.

Figure 6:
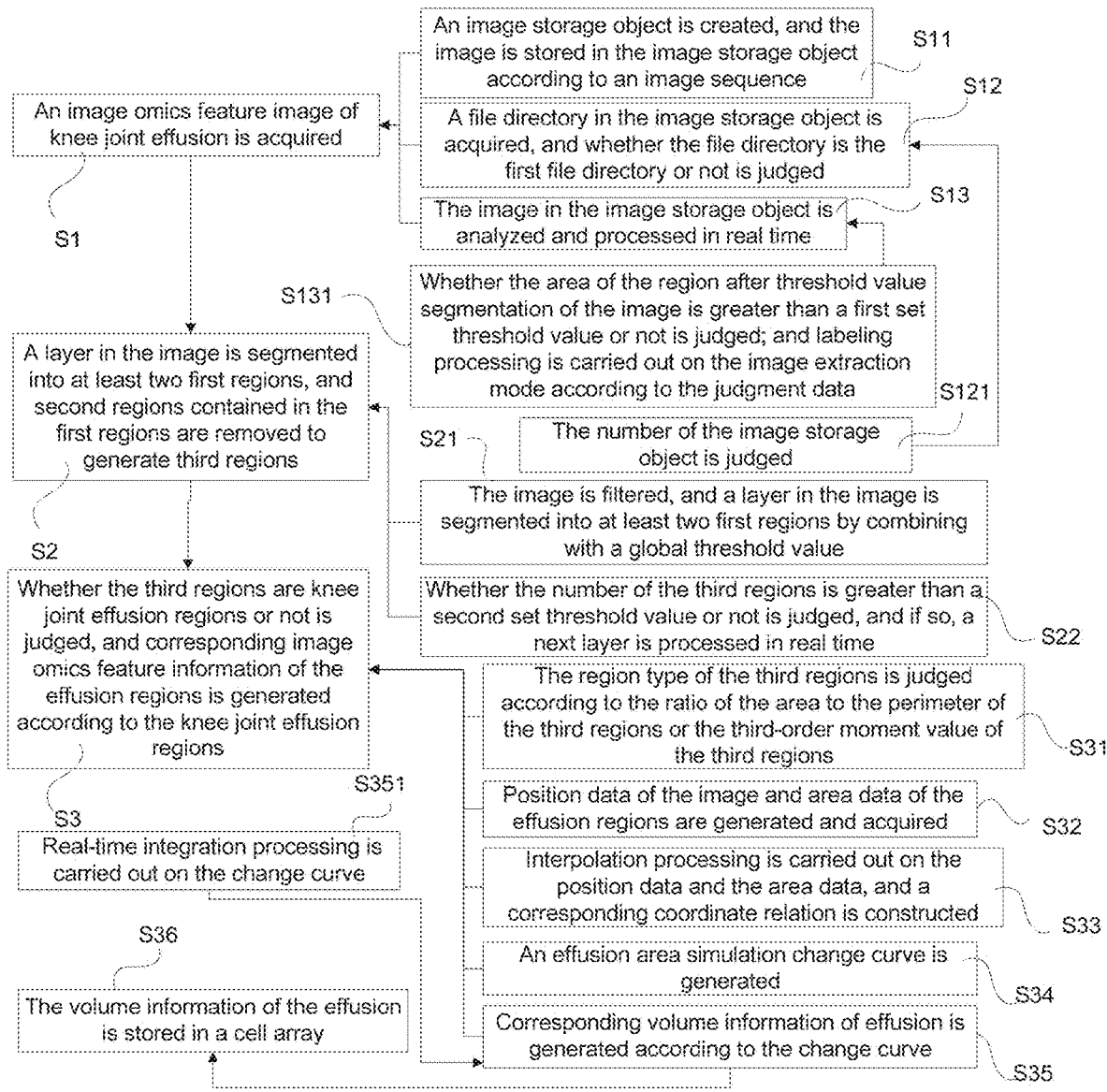
FIG. 6 is a flowchart of an extraction method for radiomics feature information of knee joint effusion.

As shown in FIG. 6, the disclosure provides an extraction method for radiomics feature information of knee joint effusion, which specifically includes the following steps.

In S1, an radiomics feature image of knee joint effusion is acquired.

In S2, a layer in the image is segmented into at least two first regions, and second regions contained in the first regions are removed to generate third regions.

In S3, whether the third regions are knee joint effusion regions or not is judged, and corresponding radiomics feature information of the effusion regions is generated according to the knee joint effusion regions.

In S1, an radiomics feature image of knee joint effusion is acquired, which specifically includes the following steps.

In S11, an image storage object is created, and the image is stored in the image storage object according to an image sequence.

In S12, a file directory in the image storage object is acquired, and whether the file directory is the first file directory or not is judged.

In S13, the image in the image storage object is analyzed and processed in real time.

In S12, a file directory in the image storage object is acquired, which specifically includes the following step: in S121, the number of the image storage object is judged.

In S13, the image in the image storage object is analyzed and processed in real time, which specifically includes the following step: in S131, whether the area of the region after threshold value segmentation of the image is greater than a first set threshold value or not is judged; and labeling processing is implemented on the image extraction mode according to the judgment data.

In S2, a layer in the image is segmented into at least two first regions, and second regions contained in the first regions are removed to generate third regions, which specifically includes the following steps.

In S21, the image is filtered, and a layer in the image is segmented into at least two first regions by combining with a global threshold value.

In S22, whether the number of the third regions is greater than a second set threshold value or not is judged, and if so, a next layer is processed in real time.

A next layer is processed, specifically, the next layer is segmented by combining with a high threshold value and at least two first regions are generated.

The first regions are specifically regions generated after layer segmentation processing of the image; the second regions are specifically interference regions in the regions generated after the layer of the image is segmented; and the third regions are specifically regions generated after the second regions are removed from the first regions.

In S3, whether the third regions are knee joint effusion regions or not is judged, and corresponding radiomics feature information of the effusion regions is generated according to the knee joint effusion regions, which specifically includes the following steps.

In S31, the region type of the third regions is judged according to the ratio of the area to the perimeter of the third regions or the third-order moment value of the third regions.

The region type includes a subcutaneous fat region and an effusion region.

The calculating formula of the third-order moment is specifically as follows.

$$\zeta_i = \left[\frac{1}{N}\sum_{j=1}^{N}(P_{ij}-\mu_i)^3\right]^{1/3} \quad (1)$$

$\zeta_i$ refers to the third-order moment of the i region, N is the total number of pixels of the i region, $P_{ij}$ refers to the gray value of the jth pixel of the i region.

The step that corresponding radiomics feature information of the effusion regions is generated according to the knee joint effusion regions specifically includes the following steps.

In S32, position data of the image and area data of the effusion regions are generated and acquired.

In S33, interpolation processing is implemented on the position data and the area data, and a corresponding coordinate relation is constructed.

In S34, an effusion area simulation change curve is generated.

In S35, corresponding volume information of effusion is generated according to the change curve.

In S35, corresponding volume information of effusion is generated according to the change curve, specifically, including the following steps.

In S351, real-time integration processing is implemented on the change curve; and the formula for the integration processing is specifically as follows.

$$V=\int_0^d \text{area}(x)dx \quad (2)$$

d is the thickness of the knee joint and area(x) is an area function obtained after interpolation processing.

After S35 that corresponding volume information of effusion is generated according to the change curve, the following step is further specifically included: S36, the volume information of the effusion is stored in a cell array.

Specifically, according to an automatic extraction method for radiomics features of knee joint based on an MATLAB, first, each layer of an image is segmented into a plurality of regions, the interference of tiny noises in each region is removed, then whether each region after interference removal is an effusion region or not is judged, finally, the radiomics feature of each effusion region is calculated, interpolation processing is respectively implemented on the obtained image position and area of the effusion, an effusion area simulation change curve is drawn, then curve integration is implemented to obtain volume information, and all the extracted information is stored in a cell array of the MATLAB.

Figure 1:
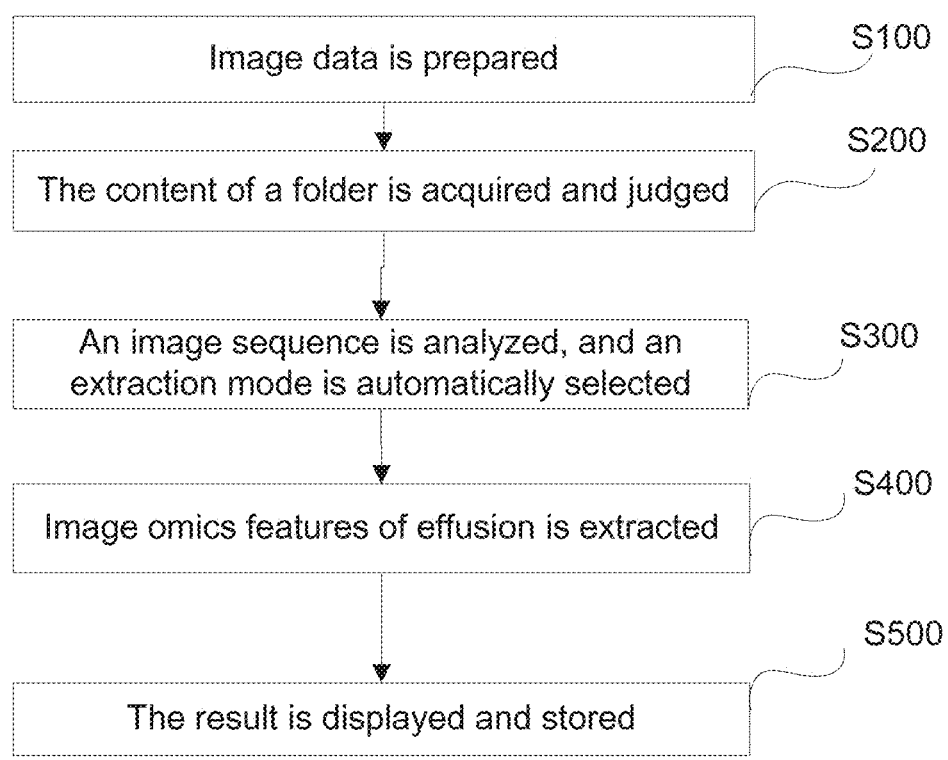
FIG. 1 is a flow diagram of an embodiment of an automatic extraction method for radiomics features of knee joint based on a MATLAB according to the disclosure.

As shown in FIG. 1, an automatic extraction method for radiomics features of knee joint based on a MATLAB platform according to the embodiment of the disclosure, which specifically includes the following steps.

In S100, image data is prepared, specifically, an image sequence is stored in a single folder, and the requirements of the image sequence are as follows: 1, the image is obtained by a single examination of a patient, 2, the image is an MRI PDW coronal image of the knee joint, 3, the length of the sequence is not limited, and 4, the resolution of the image is not limited; and if the information of a plurality of cases needs to be obtained at a time, the image sequence of each case should be stored according to the step, and all single files are put into an empty folder.

In S200, the content of the folder is acquired and judged, specifically, a user inputs the address of the folder in GUI generated by MATLAB, and clicks and loads, a system acquires information of the folder and makes judgment, and the judgment process is as follows.

In Sa201, a directory under the folder is read for the first time.

In Sa202, whether the obtained first directory is the previous directory or not is judged, and if so, Sa3 is executed according to the directory obtained for the first time; otherwise, S300 is executed according to the address of the folder.

A system acquires information of the folder, refers to information acquired from the image, including an image gray level matrix and metadata, and the metadata includes but is not limited to case basic information, shooting parameters, time and position information of the image.

In S300, an image sequence is analyzed, and an extraction mode is automatically selected, which specifically refers to: a first image is acquired, if the first image meets the condition, the extraction mode is set to be 1, and otherwise, the extraction mode is set to be 0; the condition refers to that the area of the region obtained by implementing threshold value segmentation on the global region with a low threshold value is greater than a set value (a first set threshold value), the set value is a pixel gray threshold value, the threshold value segmentation refers to that when the pixel gray value in the image is smaller than the threshold value, the pixel gray value is set to be 0, the number of pixels which are not zero is counted and multiplied with the pixel area to obtain the effusion area, and the set threshold value may be 550.

In S400, radiomics features of effusion is extracted, which specifically refers to: first, each layer of an image is segmented into a plurality of regions, the interference of image noises in each region is removed, then whether each region after interference removal is an effusion region or not is judged, finally, the radiomics feature of each effusion region is calculated, interpolation processing is respectively implemented on the obtained image position and the area of the effusion region, an effusion area simulation change curve is drawn, curve integration is implemented to obtain volume information, and all the extracted information is stored in a cell array of the MATLAB.

Furthermore, the operation that each layer of an image is segmented into a plurality of regions, and the interference of image noises in each region is removed specifically refers to: first, the a image is filtered, entering of a first layer is implemented, the first layer is segmented into a plurality of regions with a low threshold value (global threshold value), then the interference of the image noises in each region is removed by implementing opening operation (erosion followed by dilation) in morphological operation, in this case, if the number of the regions obtained in the first layer is greater than a set value (a second set threshold value), the set value is the threshold value (10) of the number of the regions, and the number of the regions is the number of regions with removal of the interference regions; entering of the next layer is implemented, finally, a second layer is segmented into a plurality of regions with a high threshold value, then the interference of the image noises in each region is removed by implementing opening operation in morphological operation, if the number of the regions obtained in the second layer is greater than a set value, entering of the next image layer is implemented, and so on until all layers of the image are processed, the low threshold value is 550, and the high threshold value is 850; for example, if the image has two layers, after the image is filtered, entering of the first layer is implemented, the first layer is segmented with a global threshold value (low threshold value: 550), then opening operation in morphological operation is executed, interference of the image noises is removed, if the number of the obtained regions is greater than a set value (10), entering of the second layer is implemented, then the low threshold value is converted into the high threshold value (850), and the rest of the operations are the same as that of the first layer.

Figure 2:
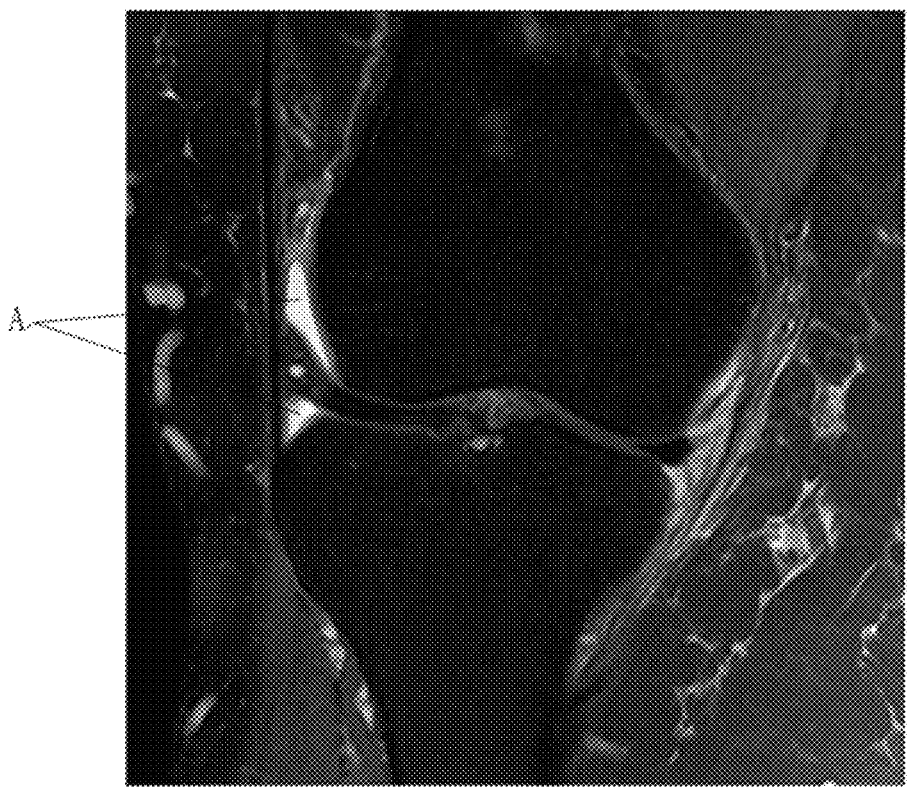
FIG. 2 is a schematic diagram of an effusion region obtained after radiomics feature extraction on effusion according to an embodiment of an automatic extraction method for radiomics features of knee joint based on a MATLAB according to the disclosure.
Figure 3:
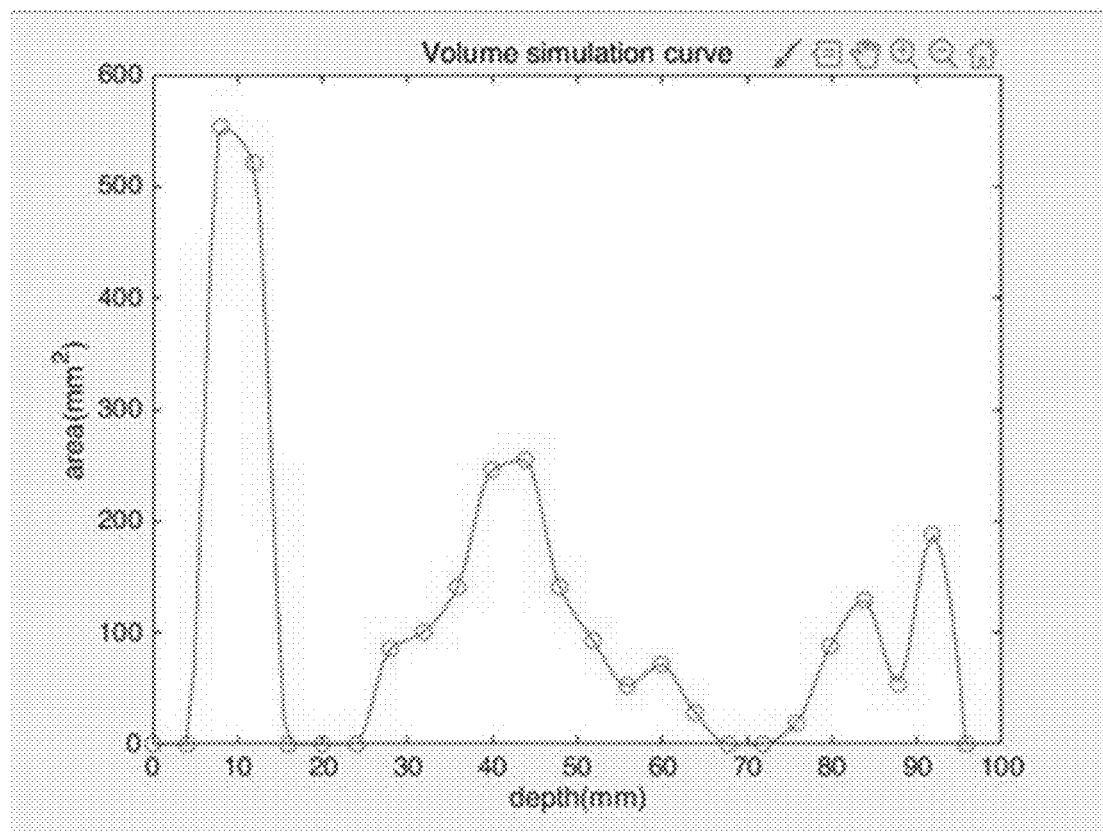
FIG. 3 is an effusion area simulation change curve obtained after radiomics feature extraction on effusion according to an embodiment of an automatic extraction method for radiomics features of knee joint based on a MATLAB according to the disclosure.

The operation that whether each region after interference removal is an effusion region or not is judged specifically refers to: at least one of the following judgments is implemented on each obtained region after interference removal (preferably, the following two judgments are executed in sequence); when the ratio of the area to the perimeter of the region is smaller than or equal to a set value (the set value of the first layer is 4.5 and the set value of the second layer is 10), the region is judged as a subcutaneous fat region, and when the ratio of the area to the perimeter of the region is greater than a set value, the region is judged as an effusion region (shown as A in FIG. 2); and when a third-order moment of the region is smaller than a set value (the set value is 0), the region is judged as an effusion region, and when the third-order moment of the region is greater than or equal to the set value, the region is judged as a subcutaneous fat region, and the formula of the third-order moment is as follows.

$$\zeta_i = \left[ \frac{1}{N} \sum_{j=1}^{N} (P_{ij} - \mu_i)^3 \right]^{1/3},$$

$\zeta_i$ refers to the third-order moment of the i region, N is the total number of pixels of the i region, $$\mu_i = \frac{1}{N} \sum_{j=1}^{N} P_{ij},$$

$P_{ij}$ refers to the gray value of the jth pixel of the i region.

The operation that the radiomics feature of each effusion region is calculated refers to: the radiomics features of each effusion region are calculated by adopting existing functions graycoprops ( ) and statxture ( ) of matlab, including gray level features and gray level co-occurrence matrix features; and the gray level features include area, contrast ratio, maximum value, average value, standard deviation, smoothness, third-order moment, consistency and entropy, and the gray level co-occurrence matrix features include contrast ratio, correlation, energy, co-occurrence degree and entropy.

The operation that interpolation processing is respectively implemented on the obtained image position and area of the effusion regions, and an effusion area simulation change curve is drawn specifically refers to: the positions of the plurality of obtained images and the area of the effusion regions are processed, a coordinate system is established by taking a value obtained after interpolation processing of the shot depth as an x axis and taking a value obtained after interpolation processing of the measured area as a y axis, and the effusion area simulation change curve is obtained.

The operation that curve integration is implemented to obtain volume information specifically refers to: volume information is obtained through calculating according to formula $V=\int_0^d area(x)dx$, d is the thickness of the knee joint, and area (x) is an area function obtained after interpolation.

In addition, in the automatic extraction method for radiomics features of knee joint based on a MATLAB according to the embodiment of the disclosure, after S400, further including S500, the result is displayed and stored, specifically as follows.

The name, height, weight, shooting date, and volume data of knee joint effusion are displayed on a GUI.

All the information is sequentially stored into an Excel worksheet (xlsx format), and the Excel worksheet is stored in a tested folder.

A message box pops up to prompt extraction success, and the obtained storage address of the data is obtained.

The automatic extraction method for radiomics features of knee joint based on a MATLAB according to the disclosure will be further described by way of specific embodiments.

Measurement Tool User Interface

Figure 4:
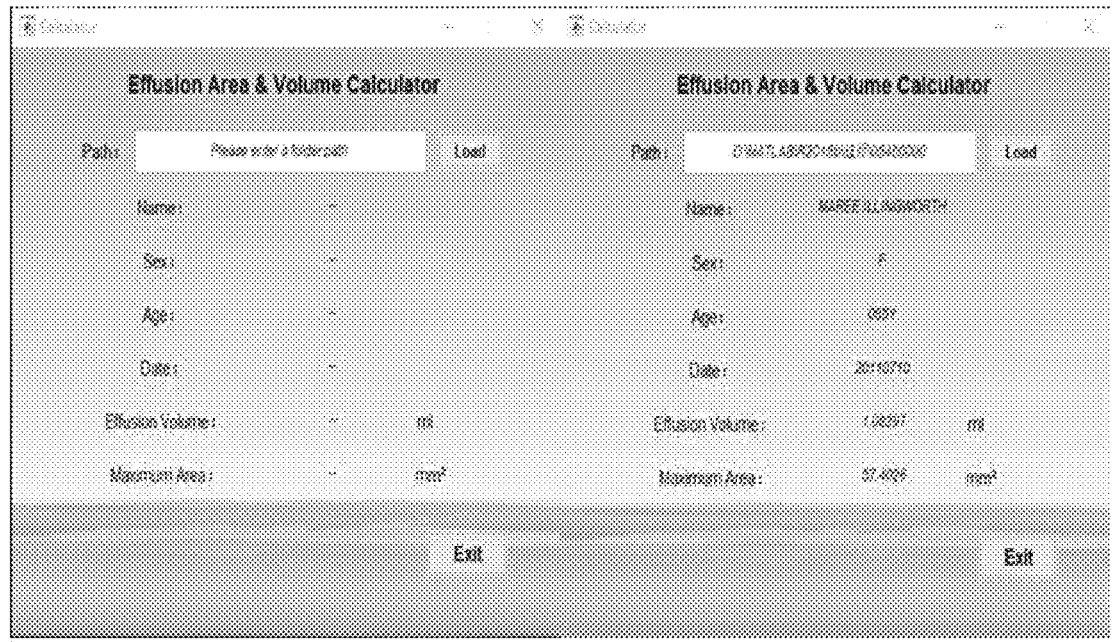
FIG. 4 is a GUI interface in an embodiment of an automatic extraction method for radiomics features of knee joint based on a MATLAB platform according to the disclosure, including: (A) file input, (B) patient information and extraction result display, (C) storage information prompt, and (D) storage information prompt when multiple cases are extracted.
Figure 4:
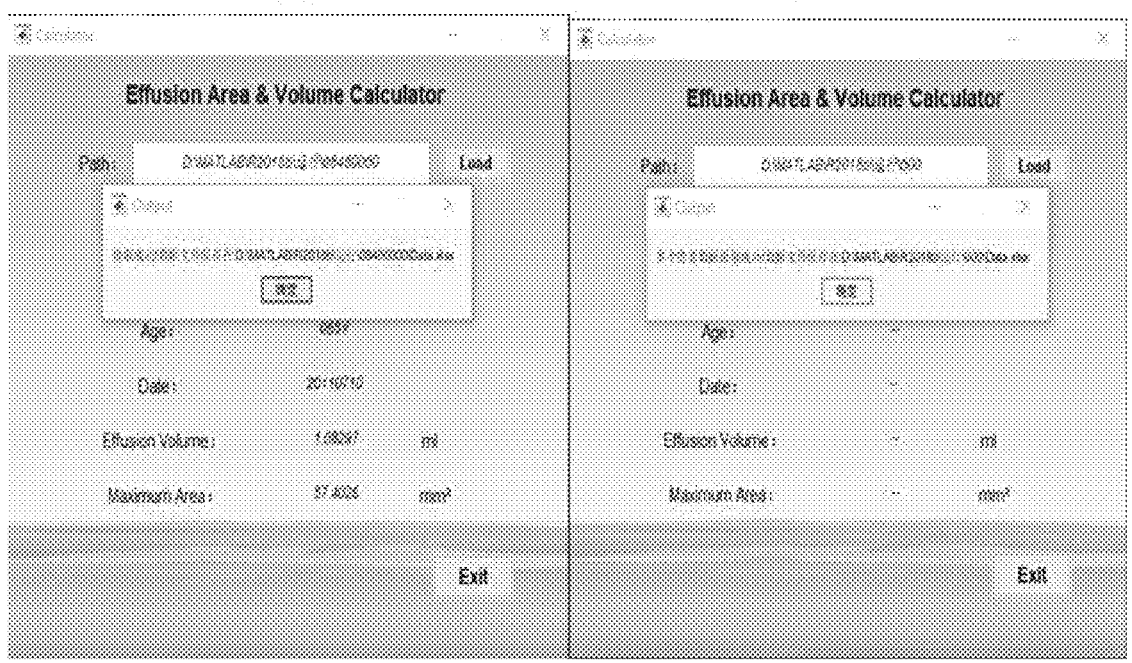

Based on a MATLAB platform, a GUI for automatically extracting radiomics features of knee joint effusion is generated. A button, a text editor and a static text box are the primary controls on the GUI interface. A user may complete measurement work through the controls. The GUI interface "FIG. 4(A)" is opened, a single patient folder path or a path containing folders of a plurality of patients (one folder for each patient independently) is input in the text editor, and execution is started by clicking the "load" button. The execution steps are as follows: the path is read, the number of the folders under the path is judged, if the number of the folders is 0, namely an MRI Proton Density Weighted (PDW) sequence image of knee joint is under the path, the image is read, preprocessing and analyzing are implemented on the image, patient information is acquired, the area and volume of effusion are calculated, all the information is sequentially stored into an Excel worksheet (xlsx format) under the path, the basic information "FIG. 4(B)" of the patient, and the maximum values of the effusion volume and the effusion area are displayed on the GUI, a window pops up for prompting a storage data path "FIG. 4(C)", and successful extraction is displayed; and if the number of folders is greater than 0, it is indicated that MRI images of a plurality of patients are under the path, the steps are similar to those described above, reading and processing are implemented in several times, but patient information is not displayed on the interface, and finally, the data is stored in an Excel worksheet at one time and a message box "FIG. 4(D)" pops up.

Case Data

A total of 151 patients were enrolled in the study, 77 women, and essentially the same number of males and females, with a mean age of 63.2 (standard deviation: 7.7) years old, and the general clinical characteristics and measured data of the study samples are described in Table 1.

TABLE 1

General clinical characteristics of study samples

|  | Characteristics |
|---|---|
| Age (y) | 63.2(7.7) |
| Female (%) | 51.0% |
| BMI (kg/m$^2$) | 29.6 (5.3) |
| Knee joint pain progression (%) | 26.9% |
| Effusion volume (ml) obtained through semi-automatic measurement | 4.3(4.3) |
| Maximum effusion volume (mm$^2$) obtained through automatic measurement | 335.5(287.9) |
| Effusion volume (ml) obtained through automatic measurement | 6.6(5.3) |

Note:
continuous variables are expressed as mean +/− standard deviation, and dichotomous variables are expressed as percentage.

Measurement Repeatability

The Interclass Correlation Coefficient (ICC) range for the automatic measurement of 15 parameters is 0.9 to 1 (Table 2), all between 0.81 and 1.00, showing excellent repeated measurement consistency for the automatic measurement method.

TABLE 2

Inter-observer consistency

| Parameters | ICC | 95% CI |
|---|---|---|
| Effusion area average | 1 | 1 < ICC < 1 |
| Effusion volume | 0.998 | 0.997 < ICC < 1 |
| Image gray maximum average | 0.999 | 0.999 < ICC < 1 |
| Image gray average | 1 | 0.999 < ICC < 1 |
| Image gray standard deviation average | 1 | 1 < ICC < 1 |
| Image contrast average | 1 | 1 < ICC < 1 |
| Image smoothness average | 0.999 | 0.999 < ICC < 1 |
| Image third-order moment average | 1 | 1 < ICC < 1 |
| Image consistency average | 0.945 | 0.904 < ICC < 0.968 |
| Image entropy average | 1 | 0.999 < ICC < 1 |
| Gray co-occurrence image contrast average | 0.999 | 0.998 < ICC < 0.999 |
| Gray co-occurrence image self-correlation average | 0.451 | 0.197 < ICC < 0.648 |
| Gray co-occurrence image energy average | 0.994 | 0.99 < ICC < 0.997 |
| Gray co-occurrence image co-occurrence average | 0.976 | 0.958 < ICC < 0.986 |
| Gray co-occurrence image entropy average | 0.998 | 0.997 < ICC < 0.999 |

Note:
ICC, interclass correlation coefficient

Comparison of Automatic and Manual Measurements and Correlation of Results

Figure 5:
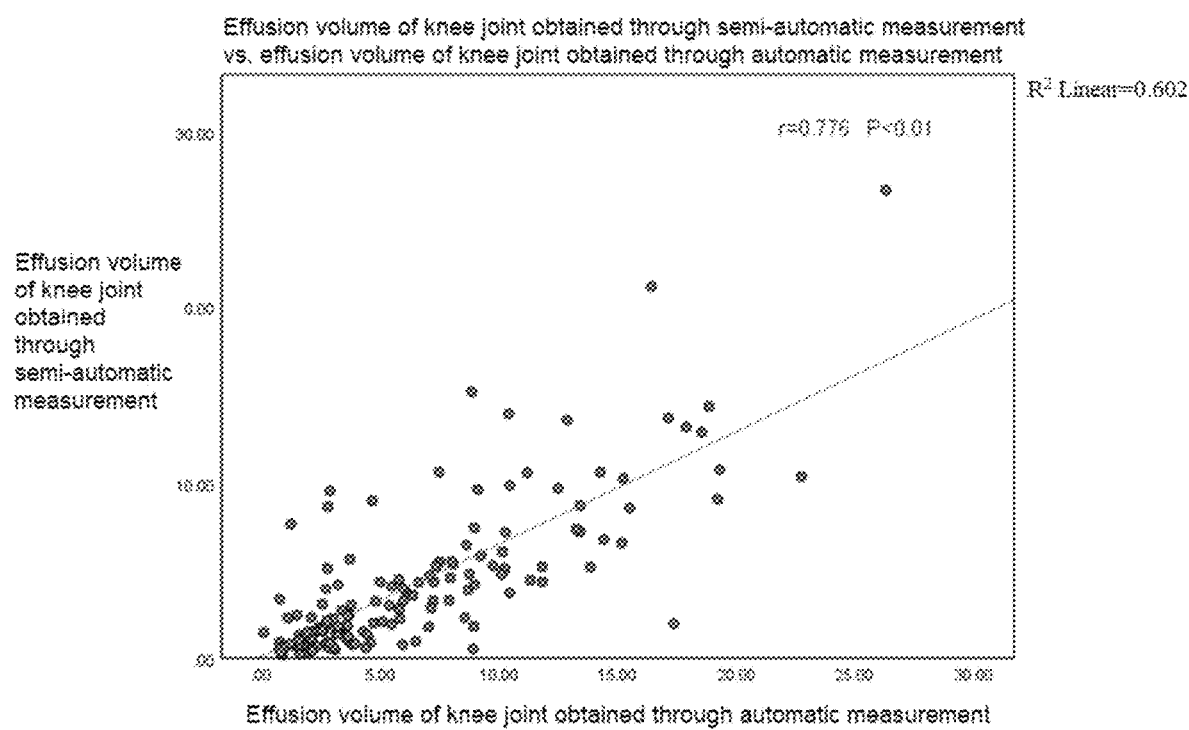
FIG. 5 is a dependent scatter plot of volume of effusion automatically and semi-automatically measured in an embodiment of an automatic extraction method for radiomics features of knee joint based on a MATLAB platform according to the disclosure.

With an automatic measurement tool, approximately 6.5 seconds are taken for each subject on average (as time is consumed when a single patient is displayed on the GUI interface), approximately 5.5 seconds are taken to measure 50 patients in bulk, and with a semi-automatic measurement tool (Osirix calculation after manual delineation), approximately 15 minutes are taken for each subject on average. Pearson correlation analysis shows that the results of the automatic measurement method and the semi-automatic measurement method are highly correlated, and the correlation coefficient r=0.79>0.6, and P<0.05. (FIG. 5)

To sum up, through the automatic extraction method for radiomics features of the knee joint based on an MATLAB according to the disclosure, magnetic resonance may be implemented on the knee joint, meanwhile, the volume and area of the effusion and various radiomics information may be quantitatively and automatically extracted, thus effusion information (including more than ten items such as volume, maximum area, gray value and the like) in the MRI image of the knee joint is realized, the method is fast in speed (average time consumption is 5 seconds), high in accuracy, good in repeatability, free of platform limitation, and convenient and fast, the defects of time consumption, labor consumption, poor measurement consistency and poor actual feasibility in the traditional manual measurement or subjective estimation method adopted by doctors in the prior art are overcome, the extracted volume and area of effusion may be used for clinical diagnosis of knee osteoarthritis and judgment of disease progression and prognosis, the extracted radiomics information may be used for constructing an accurate disease transformation prediction model or other scientific researches related to radiomics, and the method is worthy of being popularized in personnel engaged in the field of magnetic resonance image research.

The foregoing is merely preferable implementation modes of the disclosure, it should be pointed out that those of ordinary skill in the art can also make some modifications and improvements without departing from the principle of the disclosure, and these modifications and improvements all fall within the scope of protection of the disclosure.

What is claimed is:

1. An extraction method for radiomics feature information of knee joint effusion, comprising following specific steps:
acquiring a radiomics feature image of knee joint effusion, the acquiring comprising:
segmenting each layer of the image into a plurality of regions,
removing an interference of image noises in each region,
determining an effusion region in the each region after the interference of image noises is removed,
calculating radiomics features of the each of the effusion region,
implementing, respectively, interpolation processing on an obtained image position and an area of the each of the effusion region,
drawing an effusion area simulation change curve,
implementing an integration to obtain volume information, and
storing the volume information in a cell array of MATLAB;
the segmenting and the removing comprising:
filtering the image,
entering a first layer, and segmenting the first layer into a plurality of regions with a low threshold value,
removing the interference of the image noises in each region by implementing an opening operation in a morphological operation,
in response to the number of the regions obtained in the first layer being greater than a first set value, entering a second layer,
segmenting the second layer into a plurality of regions with a high threshold value,
removing the interference of the image noises in each region by implementing the opening operation in the morphological operation,
in response to the number of the regions obtained in the second layer being greater than a second set value, entering a next layer,
repeating the removing until all the layers of the image are processed;
segmenting a layer in the image into at least two first regions, and removing second regions contained in the first regions to generate third regions; and
determining knee joint effusion regions in the third regions, and generating corresponding radiomics feature information of the effusion regions according to the knee joint effusion regions,
wherein the step of segmenting the layer in the image into the at least two first regions, and removing the second regions contained in the first regions to generate the third regions specifically comprises the following steps:
filtering the image, and segmenting the layer in the image into the at least two first regions by combining with a global threshold value;
determining the number of the third regions is greater than a second set threshold value, processing the next layer in real time; and
processing the next layer specifically comprises: segmenting the next layer by combining with a high threshold value and generating the at least two first regions.

2. The extraction method for radiomics feature information of knee joint effusion as claimed in claim 1, wherein the step of acquiring a radiomics feature image of knee joint effusion further comprises the following steps:
creating an image storage object, and storing the image in the image storage object according to an image sequence;
acquiring a file directory in the image storage object, and determining the file directory is a first file directory; and
analyzing and processing the image in the image storage object in real time.

3. The extraction method for radiomics feature information of knee joint effusion as claimed in claim 2, wherein the step of acquiring a file directory in the image storage object further comprises the following step: determining the number of the image storage object;
the step of analyzing and processing the image in the image storage object in real time specifically comprises the following steps: determining the region area after threshold value segmentation of the image is greater than a first set threshold value; and implementing labelling processing on an image extraction mode according to a judgment data.

4. The extraction method for radiomics feature information of knee joint effusion as claimed in claim 1, wherein the first regions are specifically regions generated after layer segmentation processing of the image; the second regions are specifically interference regions in the regions generated after layer segmentation processing of the image; and the third regions are specifically regions generated after the second regions are removed from the first regions.

5. The extraction method for radiomics feature information of knee joint effusion as claimed in claim 1, wherein the first regions are specifically regions generated after layer segmentation processing of the image; the second regions are specifically interference regions in the regions generated after layer segmentation processing of the image; and the third regions are specifically regions generated after the second regions are removed from the first regions.

6. The extraction method for radiomics feature information of knee joint effusion as claimed in claim 1, wherein the step of determining knee joint effusion regions in the third regions, and generating corresponding radiomics feature information of the effusion regions according to the knee joint effusion regions specifically comprises the following step:
determining a region type of the third regions according to a ratio of the area to a perimeter of the third regions or a third-order moment of the third regions.

7. The extraction method for radiomics feature information of knee joint effusion as claimed in claim 6, wherein the region type comprises a subcutaneous fat region and an effusion region.

8. The extraction method for radiomics feature information of knee joint effusion as claimed in claim 6, wherein a calculating formula of the third-order moment is specifically as follows:

$$\zeta_i = \left[\frac{1}{N}\sum_{j=1}^{N}(P_{ij}-\mu_i)^3\right]^{1/3} \quad (1)$$

$\zeta_i$ refers to the third-order moment of the i region, N is a total number of pixels of the i region, and $P_{ij}$ refers to a gray value of the jth pixel of the i region.

9. The extraction method for radiomics feature information of knee joint effusion as claimed in claim 6, wherein the step of generating corresponding radiomics feature information of the effusion regions according to the knee joint effusion regions specifically comprises the following steps:
generating and acquiring position data of the image and area data of the effusion regions;
implementing interpolation processing on the position data and the area data, and constructing a corresponding coordinate relation; and
generating an effusion area simulation change curve, and generating corresponding volume information of effusion according to the change curve.

10. The extraction method for radiomics feature information of knee joint effusion as claimed in claim 1, wherein the step of generating corresponding radiomics feature information of the effusion regions according to the knee joint effusion regions specifically comprises the following steps:
generating and acquiring position data of the image and area data of the effusion regions;
implementing interpolation processing on the position data and the area data, and constructing a corresponding coordinate relation; and
generating an effusion area simulation change curve, and generating corresponding volume information of effusion according to the change curve.

11. The extraction method for radiomics feature information of knee joint effusion as claimed in claim 9, wherein the step of generating corresponding volume information of effusion according to the change curve further specifically comprises the following steps:
implementing real-time integration processing on the change curve; a formula for the integration processing is specifically as follows, $$V=\int_0^d \text{area}(x)dx \quad (2)$$

d is a thickness of the knee joint, and area(x) is an area function obtained after interpolation processing; and
after the step of generating corresponding volume information of effusion according to the change curve, specifically, comprising the following step: storing the volume information of the effusion in a cell array.

12. The extraction method for radiomics feature information of knee joint effusion as claimed in claim 10, wherein the step of generating corresponding volume information of effusion according to the change curve further specifically comprises the following steps:
implementing real-time integration processing on the change curve; a formula for the integration processing is specifically as follows:

$$V=\int_0^d \text{area}(x)dx \quad (2)$$

d is a thickness of the knee joint, and area(x) is an area function obtained after interpolation processing; and
after the step of generating corresponding volume information of effusion according to the change curve, specifically, comprising the following step: storing the volume information of the effusion in a cell array.

* * * * *